United States Patent
Claus et al.

(10) Patent No.: US 8,555,070 B2
(45) Date of Patent: *Oct. 8, 2013

(54) EXTERNAL INTERFACE ACCESS CONTROL FOR MEDICAL SYSTEMS

(75) Inventors: Michael J. Claus, Newport Coast, CA (US); Timothy Hunter, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1114 days.

This patent is subject to a terminal disclaimer.

(21) Appl. No.: 11/733,554

(22) Filed: Apr. 10, 2007

(65) Prior Publication Data

US 2008/0256076 A1     Oct. 16, 2008

(51) Int. Cl.
H04L 9/32     (2006.01)
(52) U.S. Cl.
USPC ............. 713/176; 713/161; 713/165; 726/22; 726/30
(58) Field of Classification Search
None
See application file for complete search history.

(56) References Cited

U.S. PATENT DOCUMENTS

| | | | |
|---|---|---|---|
| 5,987,123 A * | 11/1999 | Scott et al. | 713/165 |
| 6,106,396 A | 8/2000 | Alcorn et al. | |
| 7,124,408 B1 | 10/2006 | Parthasarathy et al. | |
| 7,412,450 B1 * | 8/2008 | Bonwick et al. | 1/1 |
| 2003/0187885 A1 * | 10/2003 | Miyazaki et al. | 707/203 |
| 2004/0003271 A1 * | 1/2004 | Bourne et al. | 713/193 |
| 2004/0248646 A1 * | 12/2004 | Canterbury | 463/29 |
| 2005/0102669 A1 * | 5/2005 | Marney et al. | 717/174 |
| 2005/0108240 A1 * | 5/2005 | Bolosky et al. | 707/9 |
| 2006/0100010 A1 * | 5/2006 | Gatto et al. | |
| 2007/0192610 A1 * | 8/2007 | Chun et al. | 713/176 |
| 2007/0276823 A1 * | 11/2007 | Borden et al. | 707/5 |
| 2008/0082960 A1 * | 4/2008 | McDougal et al. | 717/107 |
| 2009/0103902 A1 * | 4/2009 | Matsuura et al. | 386/124 |

* cited by examiner

*Primary Examiner* — Shewaye Gelagay

(74) *Attorney, Agent, or Firm* — Abbott Medical Optics Inc.

(57) ABSTRACT

A method and system of controlling access to a system in a medical environment is provided. The method includes calculating a signature value for at least one file usable with the medical system, transferring the calculated signature value to a signature file, and providing at least one signature value in the signature file and at least one associated file to a file system configured to be received by the medical system. At least one signature value and at least one associated file are inspected by the medical system to verify the associated file is a known medical software application asset. The medical system comprises an input/output data port configured to receive the external memory storage device, and an operating system capable of reading medical system data from and writing medical system data to the memory storage device.

21 Claims, 3 Drawing Sheets

EXTERNAL INTERFACE ACCESS CONTROL FOR MEDICAL SYSTEMS

BACKGROUND OF THE INVENTION

1. Field of the Invention

The present invention relates generally to the art of medical instrument systems, and more specifically to controlling access to software applications and data stored in an external file system for use in operating a safety critical medical system.

2. Description of the Related Art

Safety critical systems such as automated medical system products or surgical instrument systems may include hardware platforms providing Input/Output (I/O) data ports enabling access from outside of the instrument system. Current medical system designs such as those available from Advanced Medical Optics, Inc. provide access from outside of the system via a Universal Serial Bus (USB) I/O data port. A USB data I/O port provides an interface for connecting a USB device. Types of devices that may be connected to the USB I/O data port include a 'memory-stick' flash memory storage device, USB CD-ROM or DVD device, or a USB enabled hard drive, each providing access to a file system. To gain access to the file system stored in a USB compliant storage device, the user need only to connect the USB storage device by plugging it into the instrument system's USB host controller or connection.

Providing surgical instrument systems with open data interfaces, such as a USB I/O data port, affords designers flexibility in providing additional functionality to the end user. The increased functionality and capabilities may be realized from software applications and data residing in a USB device. Any number of individuals may have access to the system via the USB I/O data port. Persons able to access the system may include factory sales representatives, service personnel, and physicians. For example, service personnel may store software applications for use in troubleshooting, engage in calibration and diagnostics of the instrument system, transfer files between instrument host systems, or repair and upgrade the system software. Sales personnel may demonstrate new features and functionality by executing a preconfigured software application stored in a USB device. Physicians may store individual preferences, surgical procedure settings, and other configurable instrument system parameters.

A major disadvantage of such open designs is that the system becomes vulnerable to potential corruption. The primary concern involves either virus software or malicious programs that may gain access via the open external data port. When a program is executed from the USB storage device, the software can gain access to all of the resources forming the safety critical system. If a malicious program executes from the USB device file system, the program could alter or corrupt the operating system software, modify stored physicians settings, and rewrite portions of software applications required for the proper and safe operation of the instrument system. In a similar manner, a virus program may execute from the USB device file system and insert a virus into the instrument systems software. As may be appreciated, even an inadvertent change of data, let alone corruption of a mission critical program, can be devastating and even deadly in a medical system.

Today's deployed safety critical systems do not provide a sufficient level of file system access control for externally attached storage devices. Access control is paramount to fielding the highest level of safety required in an operating theater environment. Today's designers are faced with a difficult and complex implementation challenge to balance providing external interfaces open enough to allow the desired functionality to be realized, yet secure enough to ensure the integrity and continued safe operation of the instrument system.

In an attempt to mitigate unauthorized system access current designs may require the user to enter a password. Entering the proper password may allow the user access to software programs and data stored at the external device. Unauthorized system access may be implemented using physical protection to block access to the USB I/O data port on the instrument system. In this arrangement, only authorized users are supplied a key needed to unlock the physical protection device.

Password protection schemes are known to exhibit numerous disadvantages. For example, an authorized user may lose or forget their password. Once lost, it becomes necessary to install a mechanism to allow the password to be restored. These recovery mechanism can be difficult and costly to implement, and may open the system to additional vulnerabilities. Passwords may also be acquired by unauthorized users, either inadvertently or stolen, allowing access to vital corporate software and data assets. More importantly, once system access is gained via entering a valid password, any program or data stored in the external file system may be altered. A malicious program may be substituted for a valid software application stored in the file system. A compromised password can enable the user to unknowingly execute an altered or malicious program on the instrument system.

Current protection schemes using devices to physically block access to the external I/O data port may be easily compromised. Similar to password protection, only authorized users are given a key needed to unlock the physical block. The key may become lost or stolen and it is often possible to remove the physical block without the key by use of force. Like passwords, once unauthorized access is gained, the contents of the external file system may be altered or substituted.

Current designs may configure the external storage device as 'read-only' to effectively protect external file system contents. In this configuration, the instrument system may send data to the external device, but will not allow any data stored on the external device to enter the instrument system. This protection mechanism limits fielding much of the desired functionality because the 'read-only' configuration does not allow application software to execute from the external device.

Based on the foregoing, it would be advantageous to provide access control for use in safety critical systems that overcome the foregoing drawbacks present in previously known methods used in the design of safety critical systems.

SUMMARY OF THE INVENTION

According to one aspect of the present design, there is provided a method for controlling access to a medical system. The method comprises calculating a signature value for at least one file usable with the medical system, placing the calculated signature value in a signature file; and providing at least one signature value in the signature file and at least one associated file to a file system configured to be received by the medical system. At least one signature value and at least one associated file are inspected by the medical system to verify the associated file is a known medical software application asset.

According to a second aspect of the present design, there is provided a medical system configured to be used in association with an external memory storage device comprising a file system. The medical system comprises an input/output data port configured to receive the external memory storage device, and an operating system capable of reading medical system data from and writing medical system data to the memory storage device. Files in the file system of the external memory storage device are all associated with a signature value readable by the medical system to determine whether each file is permitted to be used in the medical system.

These and other advantages of the present invention will become apparent to those skilled in the art from the following detailed description of the invention and the accompanying drawings.

BRIEF DESCRIPTION OF THE DRAWINGS

The present invention is illustrated by way of example, and not by way of limitation, in the figures of the accompanying drawings in which.

DETAILED DESCRIPTION OF THE INVENTION

Figure 1:
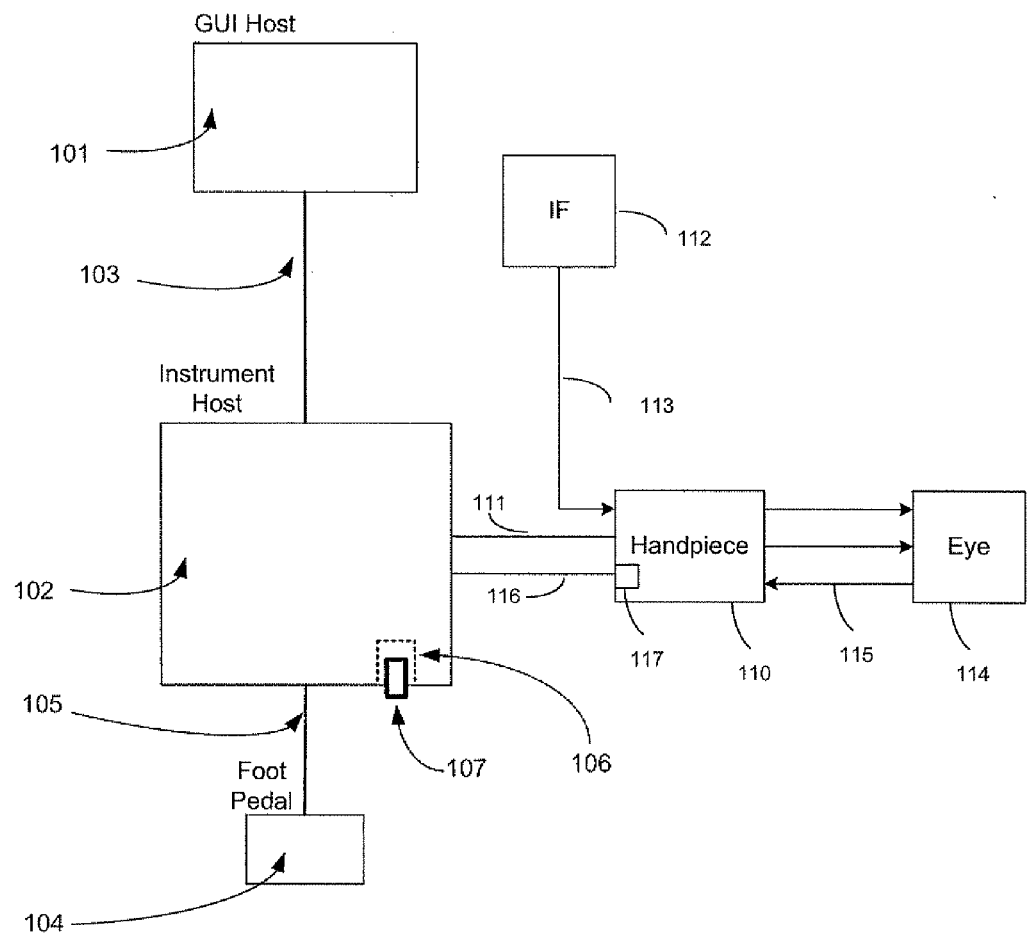
FIG. 1 is a block diagram illustrating the components and interfaces of an exemplary medical system employing a USB attached memory device in accordance with the present design.

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for controlling access to a file system resident on a memory storage device attached via an external USB compliant electrical interface in a safety critical system. The present design may provide an access control mechanism, executing on the instrument system, configured to fully identify all programs and data resident on a USB file system. The instrument system access control mechanism may inspect each program stored in the external USB memory device to determine whether access to the system is authorized and/or permissible. The inspection method involves verifying that the desired program stored in the externally connected file system is known to the instrument system manufacture as a valid software application asset. On successful validation, the present design may execute the program from the external file system affording access to the instrument system hardware and software resources. If the present design access control mechanism is unable to verify the selected program, the system may prohibit program execution and deny access to the instrument systems resources. Fundamentally, the present design may format the external file system device in a manner only known to the instrument system designers. The technique employed for formatting the external file system device may be strictly controlled by the instrument system manufacturer and does not require the external file system device format technique to be conveyed or known by the end users. In this arrangement, if the external storage device is misplaced, lost, or stolen, it may be readily replaced. If the external storage device is stolen, the file system may be accessed and the individual possessing the device may execute stored software applications. However, in this arrangement, the file system contents cannot be altered. Any attempt by unauthorized individuals to change the contents of the USB file system, by altering an existing program or substituting a malicious program for a known valid program, may be detected by the system. When an altered or substituted program is encountered, the present design may deny access to the instrument system hardware and software resources. In addition, the present design may delete or quarantine the altered or substituted program.

The present design's access control mechanism may involve digital signature techniques to identify one or more of the programs contained or stored on the external device. The present design may calculate a signature value using a cryptographic hashing algorithm and store the signature value in a signature file. In addition, the present design may encrypt the signature files by using a variant of the Data Encryption Standard (DES), Triple DES, or Advanced Encryption Standard (AES). In this arrangement, the system's use of strong encryption may virtually eliminate the risks associated with executing an invalid or unknown application program on the instrument host.

While the present design may be used in various environments and applications, it will be discussed herein with a particular emphasis on a medical or hospital environment, where a surgeon or health care practitioner performs. For example, one embodiment of the present design is a phacoemulsification/vitrectomy surgical system comprising an independent graphical user interface (GUI) module, an instrument host system module, and a controller module, such as a foot switch, to control the surgical system.

While the present design may employ various mechanisms of attaching an external memory device to the instrument, GUI host, or other subsystem, such as via a network connection realized using Ethernet, Bluetooth, or WiFi (802.11b/g), it will be discussed herein with a particular emphasis on storing file system contents on an externally attached memory device supporting the Universal Serial Bus standard.

The present design is intended to provide a basic access control mechanism for file system contents stored within an externally attached device such as a USB memory device. For simplicity, the present design arrangement and operation will be described using a single program and single signature verification file for storing the program signature value resulting from application of the hashing algorithm. However, the present design may be configured to support multiple programs, multiple signature values, and the generation of more than one signature file located on the USB memory device.

FIG. 1 illustrates a phacoemulsification/vitrectomy system in a block diagram to show the components and interfaces for a safety critical medical system in accordance with the present design. The particular embodiment illustrated in FIG. 1 contemplates that the GUI host 101 module and instrument host 102 module are connected by a serial communication cable 103 for the purposes of controlling the surgical instrument host 102 by the GUI host 101. A foot pedal 104 switch module may transmit control signals relating internal physical and virtual switch position information as input to the instrument host 102 over serial communications cable 105. Instrument host 102 may provide a USB data port 106 for attaching external devices including a USB memory storage device 107. In addition, the USB data port may be realized on the GUI host 101 or any other subsystem (not shown) that could accommodate such an input/output device.

The phacoemulsification/vitrectomy system has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to a patient's eye, or affected area or region, indicated diagrammatically by block 114. Alternatively, the irrigation source may be routed to the eye 114 through a separate pathway independent of the handpiece. Aspiration is provided to eye 114 by the instrument host 102 pump (not shown), such as a peristaltic pump, through lines 115 and 116. A switch 117 disposed on the handpiece 110 may be utilized as a means for enabling a surgeon/operator to select an amplitude of electrical pulses to the handpiece via the instrument host and GUI host. Any suitable input means, such as for example, a foot pedal 104 switch may be utilized in lieu of the switch 117.

Figure 2:
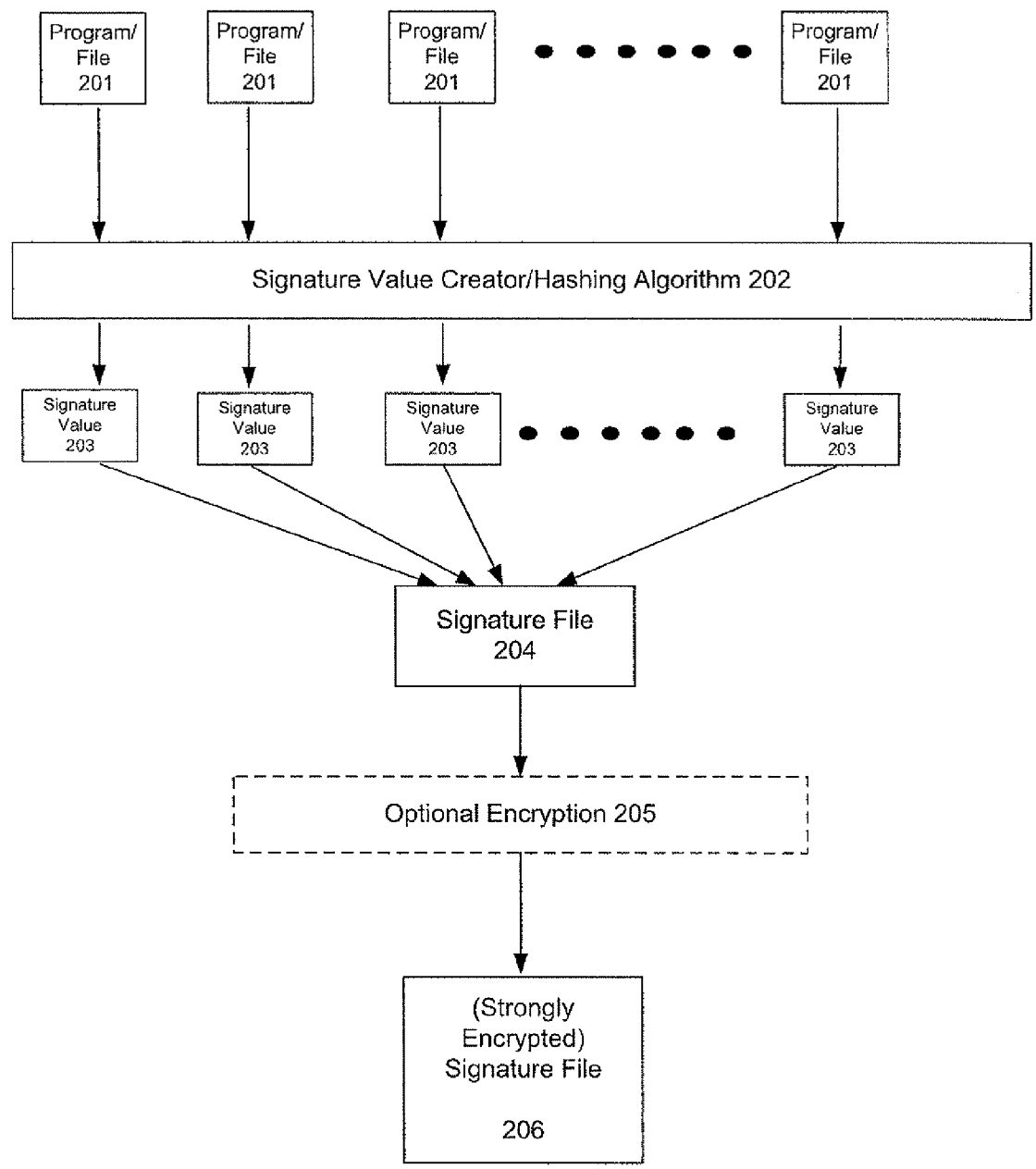
FIG. 2 is a diagram illustrating the creation of an encrypted signature file in accordance with the present design.

The apparatus and method comprising the present design access control mechanism for securing an externally connected USB file system within a safety critical system will be described. FIG. 2 is a block diagram illustrating the generation of an encrypted signature file 206 that may contain information specific to each program or data file 201 in accordance with the present design. The present design calculates a parameter, such as a signature value 203, for each program or data file 201 identified by the manufacturer for field use deployment via an externally connected USB file system. The present design may use a cryptographic hashing algorithm 202, such as the Secure Hash Algorithm-512 (SHA-512), to calculate signature value 203 for each program or data file 201. The present design may write each resultant signature value 203 into at least one signature file 204.

The SHA-512 hashing algorithm is approved by the Federal Information Processing Standard (FIPS) and is the most secure of a family of algorithms developed and utilized by the National Security Agency. Industry experts and those skilled in the art consider the SHA-512 hashing algorithm to be collision free for all practical purposes. A collision occurs if any two different programs or data files 201 result in the same calculated signature value 203. Collisions are typically expressed as a probability of collision, where a low probability of collision, as exhibited by the SHA-512 hashing algorithm, is highly desirable. The present design may provide a low probability of collision, thus the system calculated signature values remain sufficiently unique and may reliably be used to detect any possible alteration or substitution of programs or data files 201.

The present design may employ alternate hashing algorithms available for calculating signature values 203, including for example, SHA-1, Message Digest algorithm-5, Cyclic Redundancy Check-32, and linear hashing mechanisms. The appropriate algorithm may be selected by the manufacturer of the instrument host 102 based on the size and number of the files anticipated to be included in signature file 204. In a further embodiment, the present design may employ a plurality of hashing algorithms to each program or data file 201 to provide alternative hash values or multiple hash values for each program or data file 201 represented and described in the signature file 204. In this arrangement, each program or data file 201 described in the signature file 204 may be represented by an alternate hash value or multiple hash values.

Prior to writing the signature file 204 and the associated programs or data files 201 onto an USB file system in an external USE memory device 107, the present design may encrypt the signature file 204 using encryption block 205 to secure the contents from unauthorized access. The present design may encrypt the signature file 204 using encryption block 205 with a variant of the Data Encryption Standard (DES), Triple DES, or Advanced Encryption Standard (AES) developed and employed by the National Security Agency. Those skilled in the art recognize that Triple DES and AES is unbreakable without the application of prohibitively massive amounts of computer processing power, memory and time. The present design's use of strongly encrypted signature file 206 may virtually eliminate the risk associated with executing an unknown software application on the instrument host 102. The present design may be configured to use different encryption algorithms, or may apply multiple different algorithms in creating encrypted signature file 206.

Encrypting at point 205 of the signature file 204 to form an encrypted signature file 206 may prevent unauthorized or malicious users from altering the contents of this file in a manner that allows altered programs to appear to have valid signatures. The encryption signature file 206 may require the use of multiple key phrases to enable the file to be decrypted. The use of multiple key phrases is generally well known to those skilled in the art. In this arrangement, the key phrases are available only in software residing in the instrument host 102, and cannot be accessed by a user or potential hacker of the instrument system. If the encrypted signature file 206 is changed or altered, the decryption operation would fail, causing all calculated program signature values to also fail. The present design may write the encrypted signature file(s) 206 and each program or data file 201 identified for distribution onto an external file system realized using, for example, a USB memory device 107. Alternatively, in a further embodiment of the present design, the encrypted signature file(s) 206 may be written to a memory device, such as a hard drive, within the instrument host 102, GUI host 101, or other subsystem in lieu of an external USB memory device 107.

The encrypted signature file 206 may be maintained in a globally accessible file system, such as realized on a network. This arrangement may allow updates to be applied to the encrypted signature file 206 to represent legitimate program changes.

Figure 3:
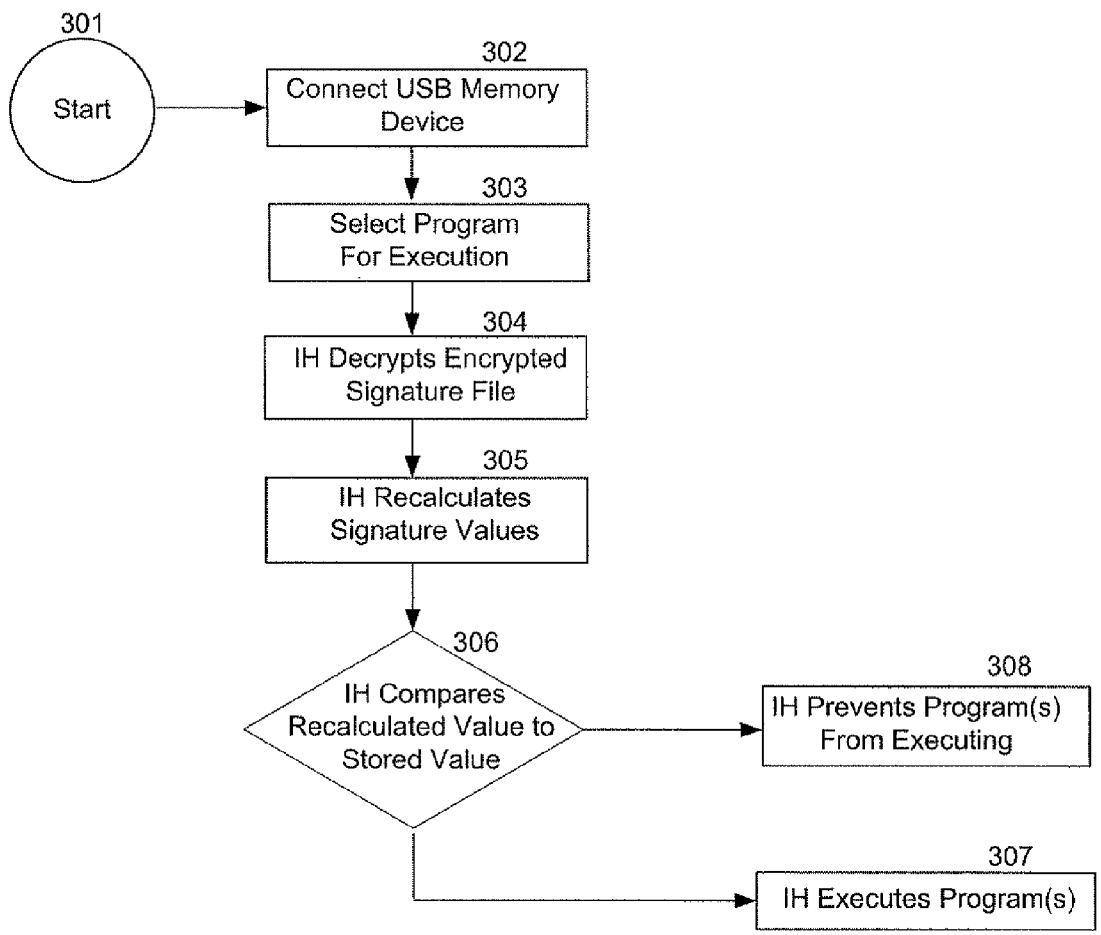
FIG. 3 is a flowchart representing the instrument host access control operations in accordance with the present design.

FIG. 3 is a flowchart illustrating the instrument host's (IH) 102 use of digital signatures. Digital signatures may be provided via an encrypted signature file 206 maintained on the USB memory device 107. The IH 102, or 'system', typically identifies and verifies each program or data file 201 and data file stored within the attached USB file system. The initial starting conditions at 301 may include an IH 102 being powered on and fully operational in an operating theater environment. The user may at point 302 connect the USB memory device 107 to the USB I/O data port 106 located on IH 102. The end-user may select a program at point 303, where the program is stored on USB memory device 107. The user may intend to execute the selected program, for example a demonstration program exhibiting new IH system functionality. The IH 102 may read and decrypt the encrypted signature file 206 at point 304 and may store the resultant decrypted signature file in system memory (not shown). The present design may decrypt the encrypted signature file 206 using the same mechanism selected during encryption, for example, a variant of the Data Encryption Standard (DES), Triple DES, or Advanced Encryption Standard (AES), typically comprising performing a reverse operation from the encrypting operation. Such decryption and encryption are typical functions offered by the aforementioned processes. The encryption signature file 206 may require the use of multiple key phrases to ensure e the file is properly decrypted. In this arrangement, the required key phrases are available only to software residing in the IH 102, and cannot be accessed by a user or potential hacker of the instrument system, or even the system creator.

The present design may be alternately be configured to employ a password mechanism to decrypt the encrypted signature file 206 in lieu of embedding the key phrase in the instrument software, as previously described. In addition, the encrypted signature values may be maintained within the program files themselves, in lieu of in a separate signature file.

The IH 102 may recalculate the signature value at 305 for each program or data file 201 to be executed. The present design may recalculate the signature value for each program or data file 201 using the same cryptographic hashing algorithm selected during encryption; for example, the present design may use SHA-512 to recalculate the signature value for each program or data file 201.

The system may compare at point 306 the recalculated signature value to the originally calculated signature value 203 previously stored at point 304. The comparison mechanism may verify if the computed signature value at point 305 is identical to the signature contained in the decrypted signature file at point 304. The present design is configure to allow execution at 307 of programs or data files 201 when the comparison mechanism yields an identical match between the recalculated signature value at point 305 and the originally calculated signature value 203 stored in signature file 204. If the IH 102 fails to find a signature file at 306, or if the requested program does not have a signature value 203 in signature file 204, or if the signature file does not match the recalculated signature value at point 305, the instrument host 102 may prevent the program from executing or gaining access to system resources at point 308.

The present design is configured to disable the system from being "boot-loaded" from a USB device. This may involve certain straightforward changes to the systems BIOS startup configuration settings, such as selecting "disable" of the ability to boot from a remote device. In addition, the present design may be configured to disable access to the system BIOS during the boot-up cycle to further protect the IH 102. One arrangement for access to the system during boot-up may involve using a password, including a variant of the system key phrases, previously described to prevent unauthorized access.

The signature files, either associated with or incorporated within programs, files, or the like enable the IH to recognize an authorized user file or program and operate on that user file or program. Limited functionality for a generally accessible and readily modified system is the result. Encryption and decryption further minimizes the likelihood that such files or programs may be employed improperly or alter the system, and thus offers an optional added level of security. Signature files for files maintained on file systems of external devices, such as USB devices, may be calculated either on the medical system or on a device external to the USB device using the same hashing algorithm or signature file creation mechanism as is employed on the medical system. Encryption may also be performed at the system or on a system configured to use the appropriate encryption data and processing. Decryption and determination of whether the signature file is acceptable are typically done on the medical system.

The design presented herein and the specific aspects illustrated are meant not to be limiting, but may include alternate components while still incorporating the teachings and benefits of the invention. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A method for controlling access to a medical system, comprising:

calculating, at a computing device, a plurality of signature values for at least one file approved for use with said medical system by a party, wherein said calculating employs a plurality of hashing algorithms; and causing the computing device to provide the plurality of signature values in the signature file, wherein each signature value in the signature file is calculated for one associated file and provided with the one associated file to a file system on an external memory storage device, the one associated file deemed acceptable for use within the medical system by the party;

wherein the plurality of hashing algorithms are selected by the party based on a size and number of files anticipated to be provided in the signature file;

wherein one signature value and one associated file are configured to be received from the external memory storage device at the medical system, and the medical system is configured to decrypt the signature value using one of the plurality of hashing algorithms to produce a decrypted signature value, and compare the decrypted signature value against most recent known decrypted signature values provided to the medical system from the party, to verify the associated file is an acceptable file for use on the medical system, and further wherein the medical system verifying the associated file causes the medical system to afford access by a verified acceptable file to medical system computational resources and deny access by an unverified file to medical system computational resources;

wherein altering one from a group consisting of the signature file and the associated file on the external memory storage device results in the medical system not verifying the associated file and denying access by the associated file to medical system computational resources.

2. The method of claim 1, wherein one hashing algorithm comprises a cryptographic hashing algorithm.

3. The method of claim 1, wherein said file system comprises a Universal Serial Bus (USB) compliant file system, and further wherein said enabling the computing device to provide comprises enabling the computing device to provide at least one signature value and at least one associated file to a file system on the external memory storage device and wherein the external memory storage device comprises a USB compliant device.

4. The method of claim 1, wherein said file system conforms to at least one protocol from a group comprising an Ethernet, Bluetooth, or WiFi (802.11) network connected external file system, and further wherein said enabling the computing device to provide comprises enabling the computing device to provide at least one signature value and at least one associated file to the external memory storage device.

5. The method of claim 1, wherein said calculating comprises employing a hashing algorithm comprising at least one algorithm from a group comprising a Federal Information Processing Standard approved algorithm and a Secure Hashing Algorithm 512.

6. The method of claim 2, wherein the hashing algorithms comprise at least one from a group comprising a variant of the Data Encryption Standard (DES) and at least one variant of the Advanced Data Encryption Standard (AES).

7. The method of claim 2, wherein inspection by the medical system comprises decrypting said signature file and evaluating the signature value for each file provided.

8. The method of claim 7, wherein decrypting further comprises applying a standard identical to that used during encryption.

9. The method of claim 7, wherein evaluating comprises applying a same hashing algorithm standard as used during signature value calculation.

10. A medical system configured to be used in association with an external memory storage device comprising a file system, the medical system comprising:
    an input/output data port configured to receive a signature file comprising at least one file and a plurality of signature files from the external memory storage device; and
    a medical device maintaining and configured to employ an operating system capable of reading medical system data from and writing medical system data to said external memory storage device via the input/output data port;
    wherein the plurality of signature files in the signature file on the external memory storage device file is calculated using a plurality of hashing algorithms, the at least one file deemed acceptable for use within the medical system by a party, each signature value readable by the medical system and used to determine whether each file on the external memory storage device is permitted to have access to medical resources within the medical system;
    wherein the plurality of hashing algorithms are selected by the party based on a size and number of files anticipated to be provided in the signature file;
    and further wherein the medical device is configured to:
        decrypt the signature value using at least one of the hashing algorithms to produce a decrypted signature value;
        compare the decrypted signature value against most recent known decrypted signature values provided to the medical system and established by the party; and
        determine, based on the decrypted signature value of each file, whether each file is permitted to be used in the medical system while providing continued medical system operation wherein each permitted file is afforded access to medical device computational resources and each file not permitted is denied access to medical device computational resources;
    wherein altering one from a group consisting of the file and the signature file on the external memory storage devices results in the medical system not verifying the file and denying access by the file to medical system computational resources.

11. The system of claim 10, wherein the external memory storage device comprises a Universal Serial Bus (USB) compliant file system.

12. The system of claim 10, wherein the external memory storage device comprises a device having a file system conforming to at least one protocol from a group comprising an Ethernet, Bluetooth, or WiFi (802.11) network connected file system.

13. The system of claim 10, wherein at least one signature value is computed by the medical system.

14. The system of claim 10, wherein each signature value is computed using at least one Federal Information Processing Standard approved cryptographic hashing algorithm.

15. The system of claim 10, wherein each signature value is collected within at least one signature file.

16. The system of claim 15, wherein each signature file is encrypted using one from a group comprising at least one variant of the Data Encryption Standard (DES) and at least one variant of the Advanced Data Encryption Standard (AES).

17. A method for protecting medical system resources available on a medical device from access by unauthorized files stored in an external memory storage device, the method comprising:
    inspecting, using the medical device, a plurality of signature values associated with one file located on said external memory storage device, wherein each signature value is calculated using one of a plurality of hashing algorithms and all signature values for the one file are provided with the one file on the external memory storage device, the one file deemed acceptable for use within the medical device by a party; and
    verifying, using the medical device, one file stored within the external memory storage device is a known software application asset by causing the medical device to decrypt the signature value associated with the one file stored within the external medical device using one of the plurality of hashing algorithms, producing a decrypted signature value, and comparing the decrypted signature value with most recent known decrypted signature values established and provided to the medical system from the party;
    wherein the plurality of hashing algorithms are selected by the party based on a size and number of files anticipated to be provided in the signature file;
    wherein verifying the at least one file results in continued medical device operation wherein the medical device affords access by a verified acceptable file to medical device resources and denies access by an unverified unacceptable file to medical system resources, and wherein altering one from the group consisting of the file and the signature value on the external memory storage device results in the medical system not verifying the file and denying access by the file to medical system resources.

18. The method of claim 17, wherein at least one signature value is encrypted and contains a digital signature.

19. The method of claim 17, wherein verifying comprises comparing a verification signature value to a signature value within at least one signature file.

20. The method of claim 19, further comprising employing an evaluated file on the medical device when the verification signature value matches the signature value within at least one signature file associated with the evaluated file.

21. The method of claim 19, further comprising prohibiting, via the medical device, medical device usage of an evaluated file on the medical device when the verification signature value does not match the signature value within at least one signature file associated with the evaluated file.

* * * * *